(12) United States Patent
Kyusojin et al.

(10) Patent No.: US 11,177,032 B2
(45) Date of Patent: *Nov. 16, 2021

(54) INFORMATION PROCESSING APPARATUS, INFORMATION PROCESSING SYSTEM, AND INFORMATION PROCESSING METHOD

(71) Applicant: Sony Corporation, Tokyo (JP)

(72) Inventors: Hiroshi Kyusojin, Tokyo (JP); Seiji Miyama, Kanagawa (JP); Naoki Tagami, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,035

(22) Filed: May 6, 2019

(65) Prior Publication Data

US 2019/0258845 A1 Aug. 22, 2019

Related U.S. Application Data

(63) Continuation of application No. 15/684,496, filed on Aug. 23, 2017, now Pat. No. 10,311,280, which is a continuation of application No. 13/910,764, filed on Jun. 5, 2013, now Pat. No. 9,760,759.

(30) Foreign Application Priority Data

Jun. 22, 2012 (JP) ................................ 2012-140689

(51) Int. Cl.
*G06K 9/00* (2006.01)
*G06F 16/58* (2019.01)
*G16H 30/20* (2018.01)

(52) U.S. Cl.
CPC ............. *G16H 30/20* (2018.01); *G06F 16/58* (2019.01); *G06K 9/00127* (2013.01)

(58) Field of Classification Search
None
See application file for complete search history.

(56) References Cited

U.S. PATENT DOCUMENTS 4,998,010 A * 3/1991 Chandler ............. G06K 7/1093
235/462.04
5,202,931 A * 4/1993 Bacus ................ G01N 15/1475
382/133
5,638,459 A 6/1997 Rosenlof et al.
(Continued)

FOREIGN PATENT DOCUMENTS

JP 2009-053701 A 3/2009
JP 2011-117991 A 6/2011

OTHER PUBLICATIONS

The State Intellectual Property Office of the People's Republic of China, Notification of the Third Office Action issued in connection with Chinese Patent Application No. 2013102370136, dated Jan. 23, 2018 (41 pages).

*Primary Examiner* — Mohammad J Rahman
(74) *Attorney, Agent, or Firm* — K&L Gates LLP

(57) ABSTRACT

An information processing apparatus includes a circuitry configured to provide a slide image including a sample image and a label image which are obtained by shooting a slide, generate a first image that a specific area of the slide image is concealed, output a thumbnail image, wherein the thumbnail image is one of the slide image and the first image.

13 Claims, 14 Drawing Sheets

(56) References Cited

U.S. PATENT DOCUMENTS

| | | | |
|---|---|---|---|
| 5,978,497 A * | 11/1999 | Lee | G01N 15/1475 |
| | | | 382/133 |
| 6,101,265 A | 8/2000 | Bacus et al. | |
| 7,970,197 B2 | 6/2011 | de la Torre-Bueno | |
| 8,712,123 B2 | 4/2014 | Xia et al. | |
| 9,691,043 B2 | 6/2017 | Gurney | |
| 9,772,339 B2 | 9/2017 | Fortescue et al. | |
| 2003/0112330 A1 * | 6/2003 | Yuri | G02B 21/365 |
| | | | 348/80 |
| 2006/0009692 A1 | 1/2006 | Fukuda et al. | |
| 2007/0020697 A1 * | 1/2007 | Cualing | G01N 33/57492 |
| | | | 435/7.2 |
| 2008/0044084 A1 | 2/2008 | Lee et al. | |
| 2008/0193014 A1 | 8/2008 | Ecker et al. | |
| 2008/0240613 A1 * | 10/2008 | Dietz | G02B 21/367 |
| | | | 382/284 |
| 2009/0161930 A1 * | 6/2009 | Zahniser | G06K 9/344 |
| | | | 382/128 |
| 2010/0278425 A1 | 11/2010 | Takemoto et al. | |
| 2011/0131535 A1 | 6/2011 | Tagami et al. | |
| 2012/0002034 A1 * | 1/2012 | Matsunobu | G06K 9/00127 |
| | | | 348/79 |
| 2012/0044342 A1 * | 2/2012 | Hing | G02B 21/367 |
| | | | 348/79 |
| 2012/0242824 A1 | 9/2012 | Takahashi et al. | |
| 2012/0312957 A1 * | 12/2012 | Loney | G02B 21/245 |
| | | | 250/201.3 |
| 2015/0331886 A1 * | 11/2015 | Chen | G06F 16/5846 |
| | | | 382/175 |
| 2018/0039864 A1 | 2/2018 | Yao et al. | |

\* cited by examiner

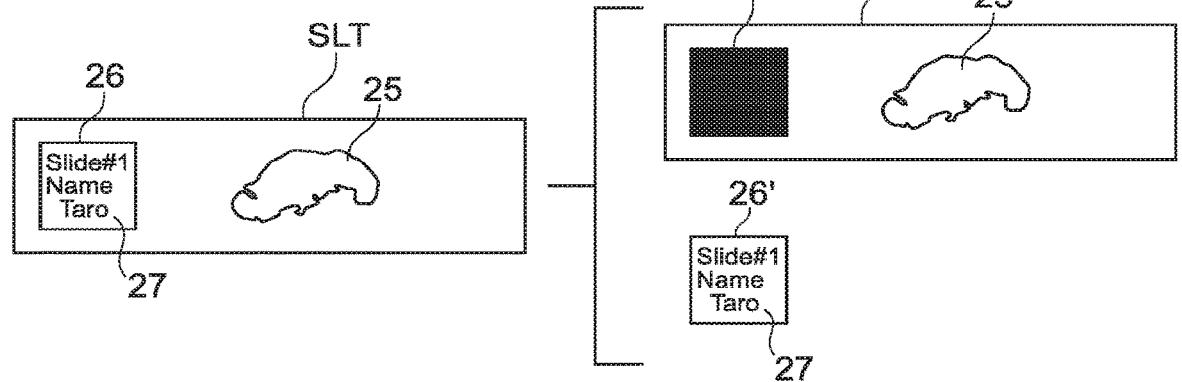
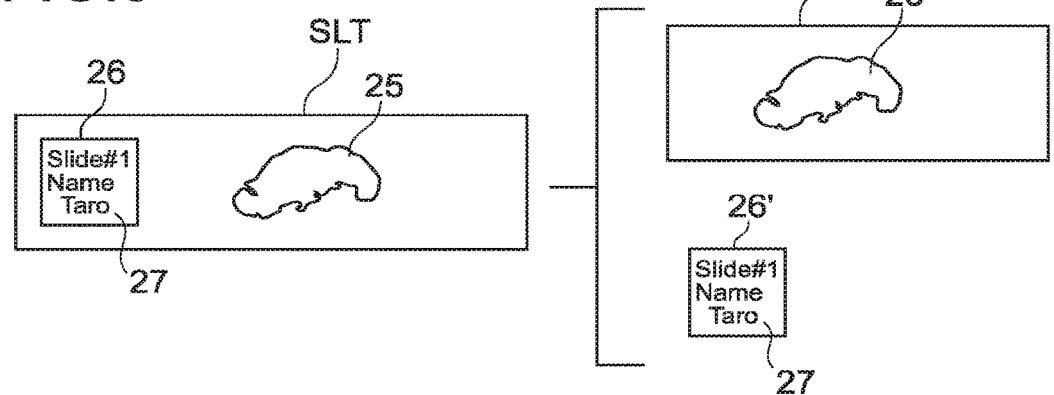
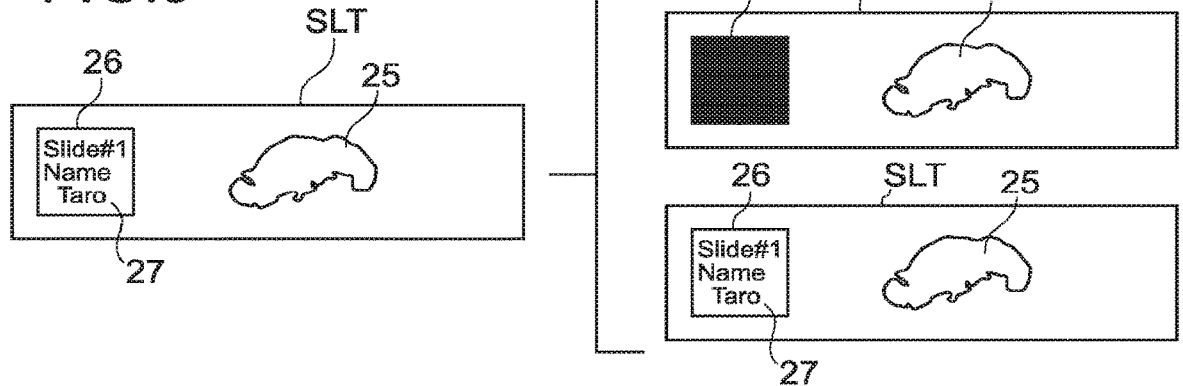

INFORMATION PROCESSING APPARATUS, INFORMATION PROCESSING SYSTEM, AND INFORMATION PROCESSING METHOD

CROSS REFERENCES TO RELATED APPLICATIONS

The present application is a continuation application of U.S. patent application Ser. No. 15/684,496, filed on Aug. 23, 2017 which is a continuation of U.S. patent application Ser. No. 13/910,764, filed on Jun. 5, 2013, which claims priority to Japanese Priority Patent Application JP 2012-140689 filed in the Japan Patent Office on Jun. 22, 2012, the entire contents of which are hereby incorporated by reference.

BACKGROUND

The present disclosure relates to an information processing apparatus, an information processing system, and an information processing method for processing an image used for a virtual microscope in a technological field of a virtual microscope used mainly in the field of medicine, pathology, or the like.

In the field of medicine, pathology, or the like, there has been proposed a virtual microscope system that digitizes images of cells, tissues, organs, or the like of a living body which are obtained by an optical microscope and allows a user such as a doctor and a pathologist to examine the tissues or the like or diagnose a patient on the basis of the digital images. The virtual microscope is capable of virtually scaling an image up and down on a computer to display the image on a display unit at a request of a user.

In a method of creating a virtual microscope slide disclosed in Japanese Patent Application Laid-open No. 2009-53701, a computer-controlled microscope is used to take a plurality of low-magnification images of a sample, fragmentize those images, and restructure the images. As a result, a macro image of the sample is created. The purpose of the creation of such a macro image is to enable a user to view the entire sample at a time and select a significant part on the image by using the entire image of the sample (see, paragraph 0042 of the specification of Japanese Patent Application Laid-open No. 2009-53701, for example).

Further, in Japanese Patent Application Laid-open No. 2011-117991, a sample held on a glass slide is read by a scanner, thereby generating images of the sample at a plurality of different magnifications (resolutions) for one sample. Furthermore, out of the images of the sample, images at predetermined low magnifications can be set as thumbnail images. The list of the thumbnail images is displayed as a screen of a thumbnail list view, and the thumbnail images are used to access real data (original image scanned) of the sample image (see, for example, paragraphs 0045 and 0052, FIG. 4, and the like of Japanese Patent Application Laid-open No. 2011-117991).

SUMMARY

It is demanded to increase the convenience and user friendliness of such a system as to display the list of thumbnail images like the thumbnail list view disclosed in Japanese Patent Application Laid-open No. 2011-117991.

In view of the above-mentioned circumstances, it is desirable to provide an information processing apparatus, an information processing system, and an information processing method capable of increasing the convenience and usability of a system that displays the list of thumbnail images.

According to an embodiment of the present disclosure, there is provided an information processing apparatus including a storage unit and an output unit.

The storage unit stores an image of a slide. The slide holds the sample and has a front surface on which the label indicating label information relating to the sample is provided. The slide image includes both images of a sample and a label which are obtained by shooting the slide.

The output unit is capable of outputting the image of the slide as a thumbnail image.

Because the slide image including both of the sample image and the label image can be displayed as a thumbnail image, a user can view the actual slide as it is on a screen. Therefore, an intuitive sense of the user is increased, and the convenience and usability are improved.

The storage unit includes a volatile storage device that temporarily stores information, in addition to a non-volatile storage device.

An output function of the output unit includes a function to perform outputting to a display apparatus for displaying.

The information processing apparatus may further include a processing unit configured to generate a cutout label image by cutting out the label image in the slide image. The storage unit may store a label-removed slide image which includes at least the sample image in the slide image and is obtained by removing the label image therefrom and the cutout label image with the label-removed slide image and the cutout label image associated with each other.

As a result, the information processing apparatus can separately store the label-removed slide image and the cutout label image (or label information, which is information indicated in the cutout label image), which is useful for the management of the information.

The processing unit may superpose a cover image for concealing the label image in the slide image on the label image in the slide image, thereby generating the label-removed slide image. The storage unit may store the label-removed slide image and the cutout label image with the label-removed slide image and the cutout label image associated with each other.

As a result, the output unit can output the thumbnail image in which the label image, i.e., the label information is concealed with the label cover image.

The processing unit may be capable of encrypting the cutout label image. The storage unit may store the label-removed slide image and an encrypted cutout label image that is subjected to the encryption with the label-removed slide image and the encrypted cutout label image associated with each other. As a result, in the case where the label information includes information highly necessary to be concealed, such as personal information, it is possible to increase the security.

Alternatively, the processing unit may be capable of encrypting the cutout label image. The processing unit may store the label-removed slide image and an encrypted cutout label image that is subjected to the encryption with the label-removed slide image and the encrypted cutout label image associated with each other.

The processing unit may be capable of decoding the encrypted cutout label image on the basis of a decoding password, and superpose the cutout label image decoded on an area where the label is provided in the label-removed slide image to restore the slide image.

As a result, the output unit can output the restored slide image as the thumbnail image.

For example, the information processing apparatus may further include a reception unit configured to receive an operation input by the user, and the processing unit can execute the restoration process in accordance with information of the operation input received by the reception unit.

The processing unit may superpose a cover image for concealing the label image in the slide image on the label image in the slide image, thereby generating the label-removed slide image. The storage unit may store the label-removed slide image and the slide image which is original with the label-removed slide image and the original slide image associated with each other.

As a result, the output unit selectively outputs the original slide image and the label-removed slide image.

For example, the information processing apparatus may further include a reception unit configured to receive an operation input by the user, and the output unit can execute the selective output process in accordance with information of the operation input obtained by the reception unit.

The processing unit may cut out a predetermined area from the slide image as a label area. Alternatively, the processing unit may cut out the label image from the slide image by an edge detection process. Alternatively, the processing unit may read the label information in the slide image by a character recognition process.

The processing unit may encrypt the label information read. As a result, in the case where the label information includes information highly necessary to be concealed, such as personal information, it is possible to increase the security.

When the slide is transparent, the storage unit may store a label-removed slide image obtained as follows with the label-removed slide image associated with the slide image. That is, by irradiating the slide with illumination light from a back surface side, which is an opposite side to the front surface of the slide, and shooting the slide from the front surface side, the sample image and the label-removed slide image are obtained so that the label information is concealed with a shadow of the label. As a result, an algorism for the cutout process of the label image is unnecessary.

According to another embodiment of the present disclosure, there is provided an information processing system including a scanner apparatus, a server apparatus, and a viewer apparatus.

The scanner apparatus includes an obtaining unit and a transmission unit. The obtaining unit is capable of shooting a slide that holds a sample and has a front surface on which a label indicating label information relating to the sample is provided and capable of obtaining an image of the slide, which includes both images of the sample and the label by the shooting. The transmission unit is capable of transmitting the image of the slide.

The server apparatus includes a storage unit, a reception unit, and a transmission unit. The storage unit is capable of storing, as a thumbnail image, the slide image transmitted from the transmission unit of the scanner apparatus. The reception unit is capable of receiving a request signal for requesting obtainment of the thumbnail image. The transmission unit is capable of transmitting the stored thumbnail image on the basis of the reception of the request signal.

The viewer apparatus includes a generation unit, a transmission unit, and a reception unit. The generation unit is capable of generating the request signal. The transmission unit is capable of transmitting the request signal generated to the server apparatus. The reception unit capable of receiving the thumbnail image transmitted from the server apparatus.

According to another embodiment of the present disclosure, there is provided an information processing system including a server apparatus and a viewer apparatus.

The server apparatus includes a storage unit, a reception unit, and a transmission unit. The storage unit is capable of storing, as a thumbnail image, an image of a slide including both images of a sample and a label which are obtained by shooting the slide, the slide holding the sample and having a front surface on which the label indicating label information relating to the sample is provided. The reception unit is capable of receiving a request signal for requesting obtainment of the thumbnail image. The transmission unit is capable of transmitting the stored thumbnail image on the basis of the reception of the request signal.

The viewer apparatus includes a generation unit, a transmission unit, and a reception unit. The generation unit is capable of generating the request signal. The transmission unit is capable of transmitting the request signal generated to the server apparatus. The reception unit is capable of receiving the thumbnail image transmitted from the server apparatus.

According to another embodiment of the present disclosure, there is provided an information processing method including storing, as a thumbnail image, an image of a slide including both images of a sample and a label which are obtained by shooting the slide, the slide holding the sample and having a front surface on which the label indicating label information relating to the sample is provided.

Then, the thumbnail image is output.

As described above, according to the present disclosure, it is possible to make the system for displaying the list of the thumbnail images more convenient and increase the usability.

Additional features and advantages are described herein, and will be apparent from the following Detailed Description and the figures.

BRIEF DESCRIPTION OF THE FIGURES

FIG. 7 is a diagram showing an example in which a label-removed glass slide image and a label image are stored as separate files;

FIG. 8 is a diagram showing an example in which the label-removed glass slide image and the label image are stored as separate files;

FIG. 9 is a diagram showing an example in which the label-removed glass slide image and an original glass slide image are stored as separate files;

DETAILED DESCRIPTION

Hereinafter, an embodiment of the present disclosure will be described with reference to the drawings.

(Structure of Information Processing System)

Figure 1:
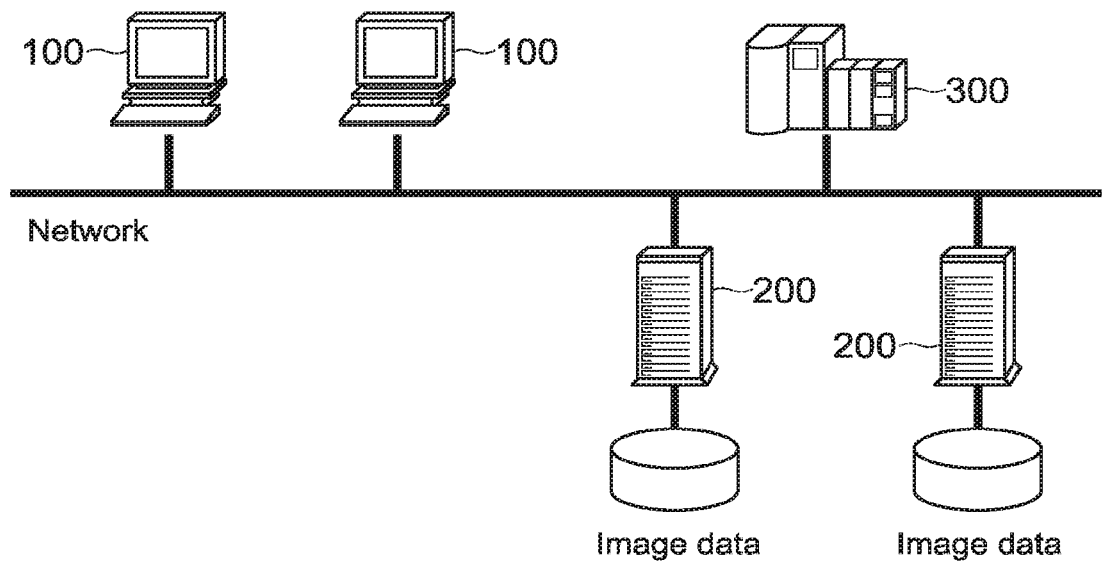
FIG. 1 is a diagram showing the structure of an information processing system according to an embodiment of the present disclosure.

FIG. 1 is a diagram showing the structure of an information processing system according to an embodiment of the present disclosure.

The information processing system is provided with a plurality of information processing apparatuses connected to a network so as to communicate with each other. As the information processing apparatus, for example, a digital pathological scanner (scanner apparatus) 300, a pathological server (server apparatus) 200, and a digital viewer terminal (viewer apparatus) 100 are provided.

Typically, the network is a LAN (local area network) and is a network in a hospital. The network may include a WAN (wide area network). Alternatively, the network may use near field communication such as infrared communication.

The digital pathological scanner 300, the digital pathological server 200, and the digital viewer terminal 100 are referred to as the scanner 300, the server 200, and the viewer 100, respectively, hereinafter.

The scanner 300 is provided with an optical microscope that takes images of a sample such as a tissue of a living body held on a transparent glass slide SLG (see, FIG. 5) as a slide and has a function as a computer. The scanner 300 may be formed of known hardware.

The server 200 basically stores images of a sample taken by the scanner 300 (entire image group (hereinafter, referred to as real image data) that is formed of an image pyramid structure 50 to be described later) and an entire image of the glass slide SLG.

The viewer 100 is a terminal apparatus operated by a user, who is a doctor typically. For example, on the basis of an operation input by the user, the viewer 100 obtains the image of the glass slide SLG stored in the server 200 or the real image data from the server 200 and displays the image or the data.

Figure 2:
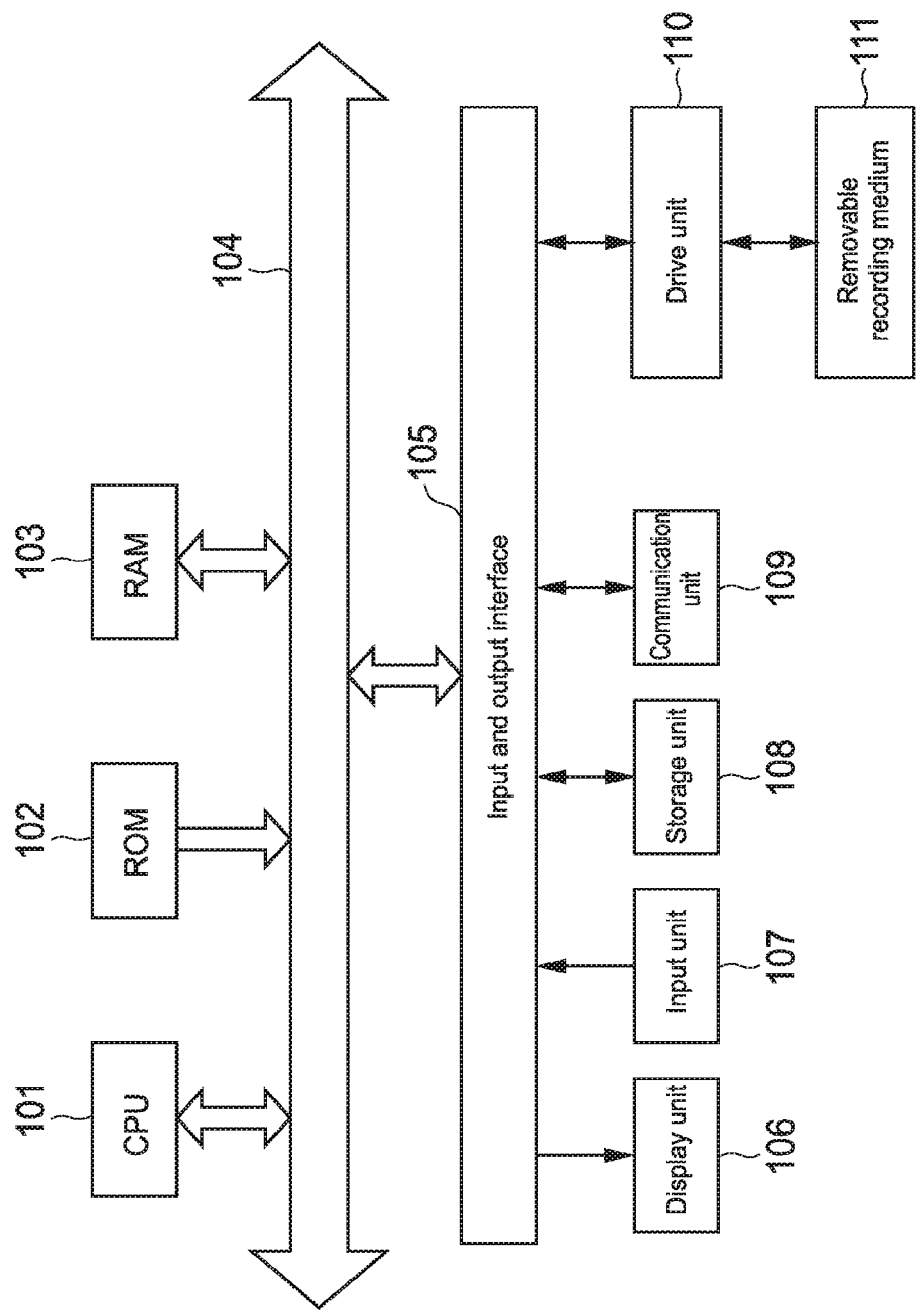
FIG. 2 is a block diagram showing the hardware structure of the information processing apparatus.

FIG. 2 is a block diagram showing a hardware structure of the viewer 100 as the information processing apparatus, for example.

Typically, the viewer 100 is formed of a PC (personal computer). The viewer 100 is provided with a CPU (central processing unit) 101, a ROM (read only memory) 102, a RAM (random access memory) 103, an input and output interface 105, and a bus 104 that connects those with each other.

To the input and output interface 105, a display unit 106, an input unit 107, a storage unit 108, a communication unit (transmission unit and reception unit) 109, a drive unit 110, and the like are connected.

The display unit 106 is a display device that uses liquid crystal, EL (electro-luminescence), a CRT (cathode ray tube), or the like.

The input unit 107 is, for example, a pointing device, a keyboard, a touch panel, or another operation device. In the case where the input unit 107 includes the touch panel, the touch panel can be integral with the display unit 106.

The storage unit 108 is a non-volatile storage device such as an HDD (hard disk drive), a flash memory, or another solid-state memory.

The drive unit 110 is a device capable of driving a removable recording medium 111 such as an optical recording medium, a floppy (registered trademark) disk, a magnetic recording tape, and a flash memory. In contrast, the storage unit 108 is often used as a device which mainly drives a non-removable recording medium and is mounted on the viewer 100 in advance.

The communication unit 109 is a communication apparatus for communicating with another device which is connectable to the LAN, the WAN, or the like. The communication unit 109 may perform wired or wireless communication. The communication unit may include a function of a modem, a router, or the like.

The scanner 300 has a function of an optical microscope and a function of a computer. The structure of hardware of the computer is the same as the structure of the viewer 100. A known structure can be used for the scanner 300.

The server 200 is also formed of a computer and only has to have the hardware structure excluding, for example, the drive unit 110 of the hardware structure of the viewer 100, for example.

The CPUs and the hardware and software necessary for the operation of the CPUs of the scanner 300, the server 200, and the viewer 100 function as a "processing unit".

(Image Structure of Sample and Display Principle Thereof)

Figure 3:
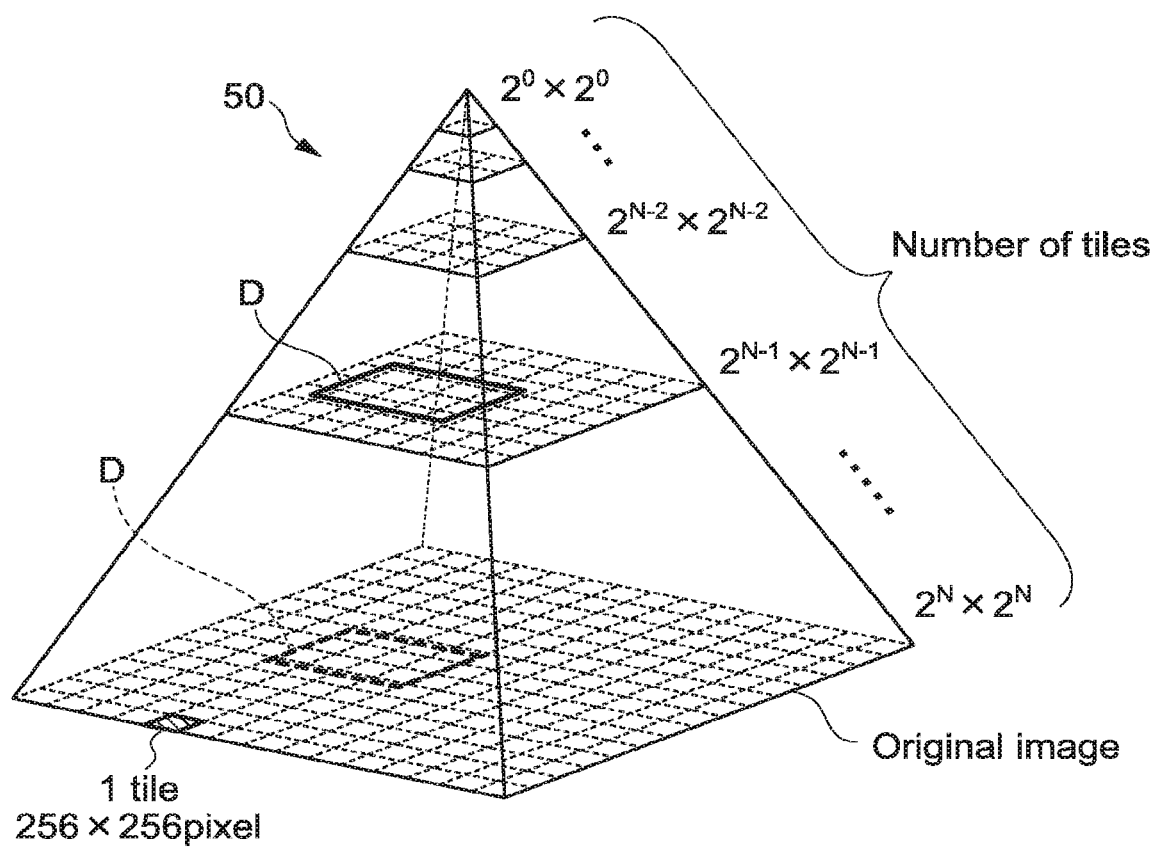
FIG. 3 is a diagram showing an image pyramid structure for explaining a display principle of real image data taken by a scanner.

Next, an image (real image data) taken by the scanner 300 and a display principle thereof will be described. FIG. 3 is a diagram showing an image pyramid structure for explaining the display principle.

In a general pathological field, an object obtained by slicing an organ, a tissue, a cell of a living body or a part thereof is a sample. As continuous slices, by continuously slicing a tissue or the like in a thickness direction thereof, a plurality of slices may be obtained. The sample sliced is stored on the glass slide SLG, and a sample 15 (see, FIG. 5) is an object to be observed with a microscope. In this embodiment, the scanner 300 having the function of the microscope scans the sample 15 on the glass slide SLG, and a digital image thus obtained is stored in the scanner 300 or the server 200.

The image pyramid structure 50 is an image group (entire image group of sample) generated at a plurality of different resolutions for the same image obtained from the sample 15 of one tissue or the like by the scanner 300. On the lowermost stage of the image pyramid structure 50, an image having the largest size is disposed, and on the uppermost stage thereof, an image having the smallest size is disposed. The resolution of the image having the largest size is, for example, 50×50 Kpixel (kilo pixel) or 40×60

(Kpixel). The resolution of the image having the smallest size is 256×256 (pixel) or 256×512 (pixel), for example.

That is, if the display unit 106 displays those images at 100%, for example (displays the images with physical dot counts equal to the pixel counts thereof), the image of the largest size is displayed to be the largest, and the image of the smallest size is displayed to be the smallest. Here, in FIG. 3, a display range of the display unit 106 is represented by D.

Figure 4:
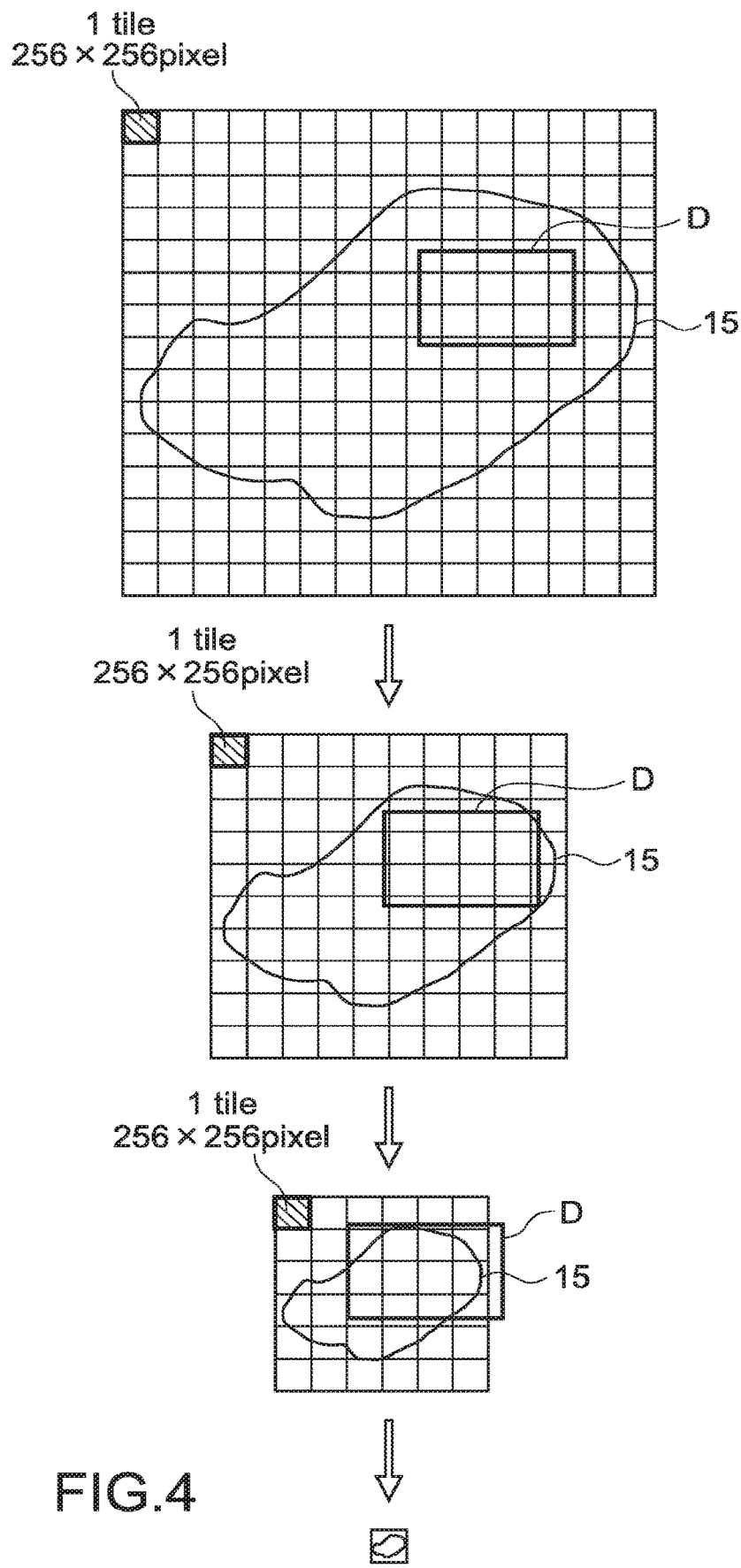
FIG. 4 is a diagram for explaining the process when an image group of the image pyramid structure is generated.

FIG. 4 is a diagram for explaining a procedure when the image group of the image pyramid structure 50 is generated.

First, the scanner 300 takes an original image as an image at a high resolution. The original image corresponds to the image having the largest size, which is the lowermost image of the image pyramid structure 50 shown in FIG. 3, that is, the image at the highest resolution.

As shown in FIG. 3, the scanner 300 or the server 200 generates a plurality of images having resolutions reduced stepwise from the image having the largest size obtained as described above and stores those images at a unit of "tile", which is a predetermined size unit, for example. The size of one tile is 256×256 (pixel), for example. The image group thus generated forms the image pyramid structure 50, and the scanner 300 stores information of the image pyramid structure 50. In actuality, the scanner 300 only has to store the images at the plurality of different resolutions and the information of the resolutions with the images and the resolutions being associated with each other. It should be noted that the image pyramid structure 50 may be generated and stored by the viewer 100 shown in FIG. 1.

The entire image group that forms the image pyramid structure 50 may be generated by a known compression method or may be generated by a known compression method for generating a general thumbnail image. Alternatively, the scanner 300 may change the magnifications from the magnification at which the original image is taken in order, actually take images of the sample at a plurality of different resolutions, and generate the image pyramid structure 50 with the entire image group thus obtained.

The viewer 100 uses application software that adopts the system of the image pyramid structure 50 to extract a desired image from the image pyramid structure 50 in accordance with an input operation by a user through the input unit 107 and output the image on the display unit 106. Specifically, the viewer 100 displays an image of any part selected by the user, out of images at any resolutions selected by the user. Through such processing, the user can obtain a feeling of observing the sample 15 while changing the magnification for observation. That is, the viewer 100 functions as a virtual microscope. A virtual magnification for observation in this case corresponds to the resolution in actuality.

Further, as described above, the scanner 300 takes an image of the entire glass slide SLG that holds the sample 15 at a predetermined magnification (resolution), thereby generating an image of the entire glass slide SLG (hereinafter, referred to as a glass slide image SLT). The left part of FIG. 7 shows an example of the glass slide image SLT obtained by the image taking. The scanner 300 stores the glass slide image SLT in the storage unit thereof or transmits the image to the server 200, and the server 200 stores the glass slide image SLT therein. The glass slide image SLT is set as a thumbnail image. In the case where the glass slide image SLT is taken at a relatively low resolution, the glass slide image SLT is set as the thumbnail image as it is.

Alternatively, in the case where the predetermined magnification is a relatively high resolution, an image obtained by compressing the glass slide image SLT may be set as the thumbnail image.

Figure 5:
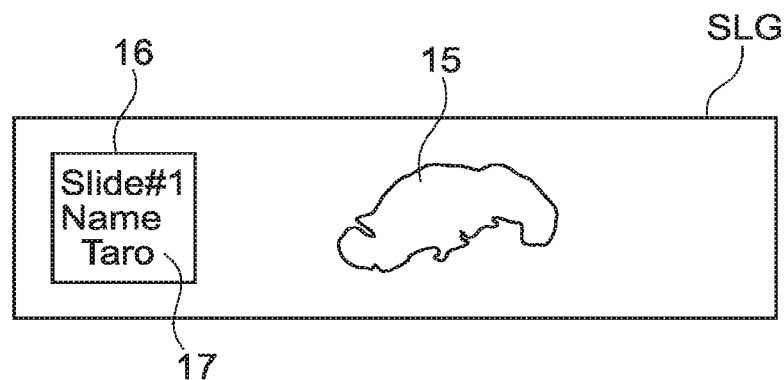
FIG. 5 is a diagram showing an example of a glass slide image obtained by shooting by the scanner.

As shown in FIG. 5, on the surface of the glass slide SLG, a label 16 on which a label information 17 is indicated may be labeled in order to increase the convenience of handling the glass slide SLG. The label information 17 is information relating to the sample 15, and characters, signs, graphics, or the like are handwritten or printed as the information. Typically, the label 16 is a paper sticker, which is self-adhesive on a surface to be stuck.

As an example of the label information, an ID (identifier) for identifying a patient whose tissue or cell is held on the glass slide SLG is given. In addition, the label information may be stain information or information that indicates an examination date and time of a patient, a scanning date and time, or the like. For example, the label 16 is labeled on the left part of the glass slide SLG in a longitudinal direction. Further, the sample 15 is stored on the center or from the center to the right part of the glass slide SLG.

The scanner 300 according to this embodiment generates the glass slide image SLT including the images of the label 16 and the sample 15 as described above. The basic characteristic of the present application lies in outputting such a glass slide image SLT as the thumbnail image by the scanner 300, the server 200, or the viewer 100.

Further, the scanner 300 or the server 200 stores the glass slide image SLT generated as described above and the real image data (entire image group that forms the image pyramid structure) corresponding thereto with the glass slide image SLT and the real image data associated with each other. As a result, as will be described later, the viewer 100 can display the thumbnail image that indicates the glass slide image SLT. When the user accesses the thumbnail image, predetermined application software for making it possible to view the real image data is activated. Thus, the user can observe the real image data.

Hereinafter, modes of a process relating to the storage of the glass slide image SLT and a process relating to the display thereof will be described. In the modes, the explanation of the same process will be simplified or omitted.

(Storing Process for Glass Slide Image SLT)

1. Mode of Storing Glass Slide Image SLT by Server 200

(A) Process in Case where Label Image is Not Encrypted

In a storing process for the glass slide image SLT, the case where a cutout image of the label image (cutout label image) is not encrypted will be described.

Figure 6:
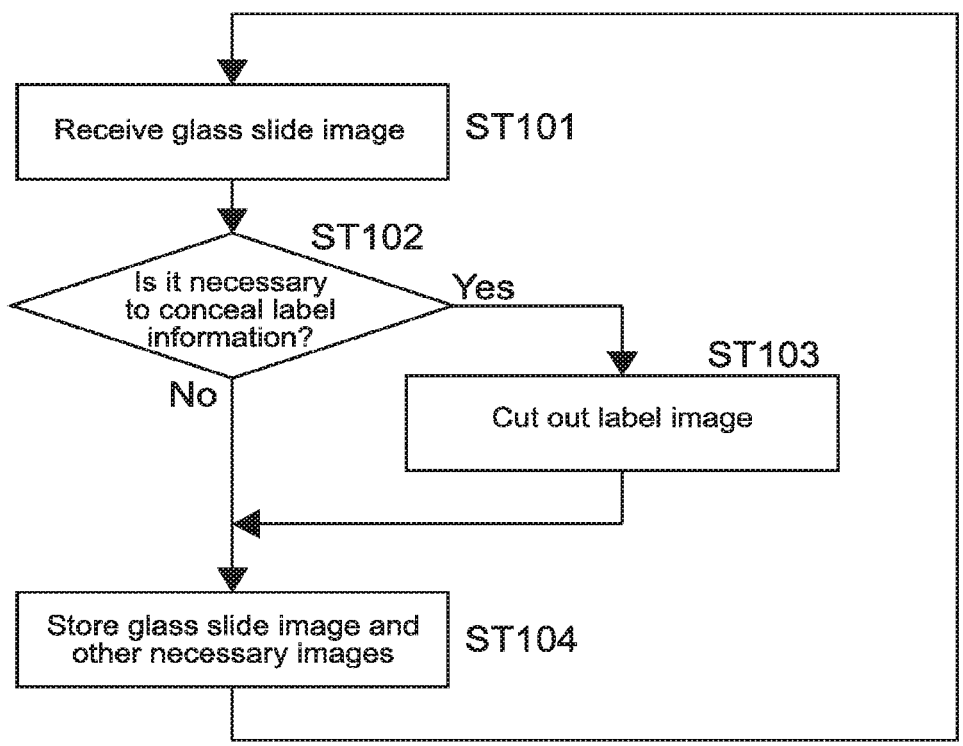
FIG. 6 is a flowchart showing the process when a server stores the glass slide image transmitted from the scanner.

FIG. 6 is a flowchart showing a process for storing the glass slide image SLT by the server 200 when the server receives the glass slide image SLT transmitted from the scanner 300. The process to be described in the following is carried out by hardware and software in cooperation with each other typically.

The server 200 receives the glass slide image SLT transmitted from the scanner 300 (Step 101). In this case, the server 200 temporarily stores the glass slide image SLT in the memory (storage unit). The server 200 determines whether it is necessary to conceal the label information in the glass slide image SLT or not (Step 102). The determination process of Step 102 may be dynamically executed in accordance with an algorithm predetermined by the server 200.

The case where the concealment is unnecessary means the case where the label information does not include private information (patient's name or the like) or the case where the label information is not indicated, for example. The server 200 can read a name as private information by a character recognition technique and check the name read against a database or determine whether the label information includes the private information or not by another algorithm.

It should be noted that a current character recognition process is not limited to the case including a step of optically reading target information like an OCR (optical character reader (recognition)) (that is, step of scanning a target object with a scanner), and a technique of converting characters in an image that does not include text information into text information is provided.

As another example of the case of being "dynamically executed", given is a mode of describing binary information relating to whether private information is included or not on the label in advance by a person and reading the binary information of the label information by the server 200.

Alternatively, the determination process of Step 102 may be statically executed, for example, a person executes the determination process.

In the case of No in Step 102, the server 200 stores the glass slide image SLT as the thumbnail image (macro image) as it is (Step 104).

<Mode of Cutout Process for Label Image>

In the case of Yes in Step 102, the server 200 cuts out a label image 26 out of the label image 26 and a sample image 25 included in the glass slide image SLT as shown in FIG. 7, thereby generating a cutout label image 26' (Step 103).

In the cutout process of Step 103, as an algorithm for causing the server 200 to recognize an area where the label image 26 is provided on the surface of the glass slide image SLT (that is, algorithm of cutout process), the following method is given.

(1) A predetermined area of the glass slide image SLT is recognized as an area of the label.

For example, at a time when a stain process for the sample is performed, in the case where the label is automatically labeled or the case where a labeling position is determined if the label is manually labeled, the area of the label is set to a fixed position and set to have a fixed size.

(2) The label image 26 in the glass slide image SLT is recognized by an edge detection process.

For example, by using a known edge detection algorithm such as a process of detecting a boundary of a luminance value binarized, it is possible to automatically detect the area of the label.

(3) The label information 17 indicated on the label 16 in the glass slide image SLT is read by the character recognition process.

This is a method of recognizing, as the label area, a circumscribed frame (for example, rectangular frame) of an area where the characters are indicated as the label information 17 by using the algorithm of the character recognition process described above.

Further, the server 200 performs the following process that comes with the process of Step 103. As shown in FIG. 7, the server 200 superposes a cover image 28 for concealing the label image of the original glass slide image SLT on the label image 26, thereby generating a glass slide image from which the label information 17 is concealed. Here, to help understanding the explanation, the glass slide image from which the label information 17 is concealed is referred to as a label-removed glass slide image (label-removed slide image), from which the label image is removed.

In the example shown in FIG. 7, the cover image 28 for concealing the label image 26 is the image is blacked out with plain black color. Of course, the cover image 28 is not limited to the block color image and may be another color (plain color or multiple colors) or may be an image including a pattern, a design, or the like.

As an image including a pattern or a design, an image obtained by blurring the label image 26 in mosaic or a picture of a key is used, for example. The picture of the key is desirably applied to the case where the label image 26 is encrypted as will be described later.

<Modes of Image Storing Process>

There are three modes of a storing process for an image by the server 200 in Step 104.

(1) The server 200 associates (ties) the cutout label image 26' generated in Step 103 with the original glass slide image SLT and stores those images as separate files.

(2) As shown in FIG. 8, the server 200 associates a label-removed glass slide image STL2 including at least the sample image, from which the area of the label image 26 is removed from the glass slide image SLT with the cutout label image 26' generated in Step 103 and stores those images as separate files.

In the case of the mode shown in FIG. 8, the server 200 may associate the original glass slide image SLT with an image including the cutout label image 26' and the label-removed glass slide image SLT2 and store those images.

(3) Alternatively, as shown in FIG. 9, the server 200 associates a label-removed glass slide image SLT1 with the original glass slide image SLT and stores those images as separate files. In this case, the cutout label image 26' generated in Step 103 only has to be stored while being associated with the label-removed glass slide image SLT1 and the original glass slide image SLT. In this case, the server 200 is capable of selectively outputting the images SLT and SLT1 upon request of the viewer.

The server 200 is in a state where the server can transmit the glass slide image SLT, the label-removed glass slide image SLT1, or the like stored as described above to the viewer 100 upon request of the viewer 100 to obtain the thumbnail image.

(B) Process in Case where Label Image can be Encrypted

Figure 10:
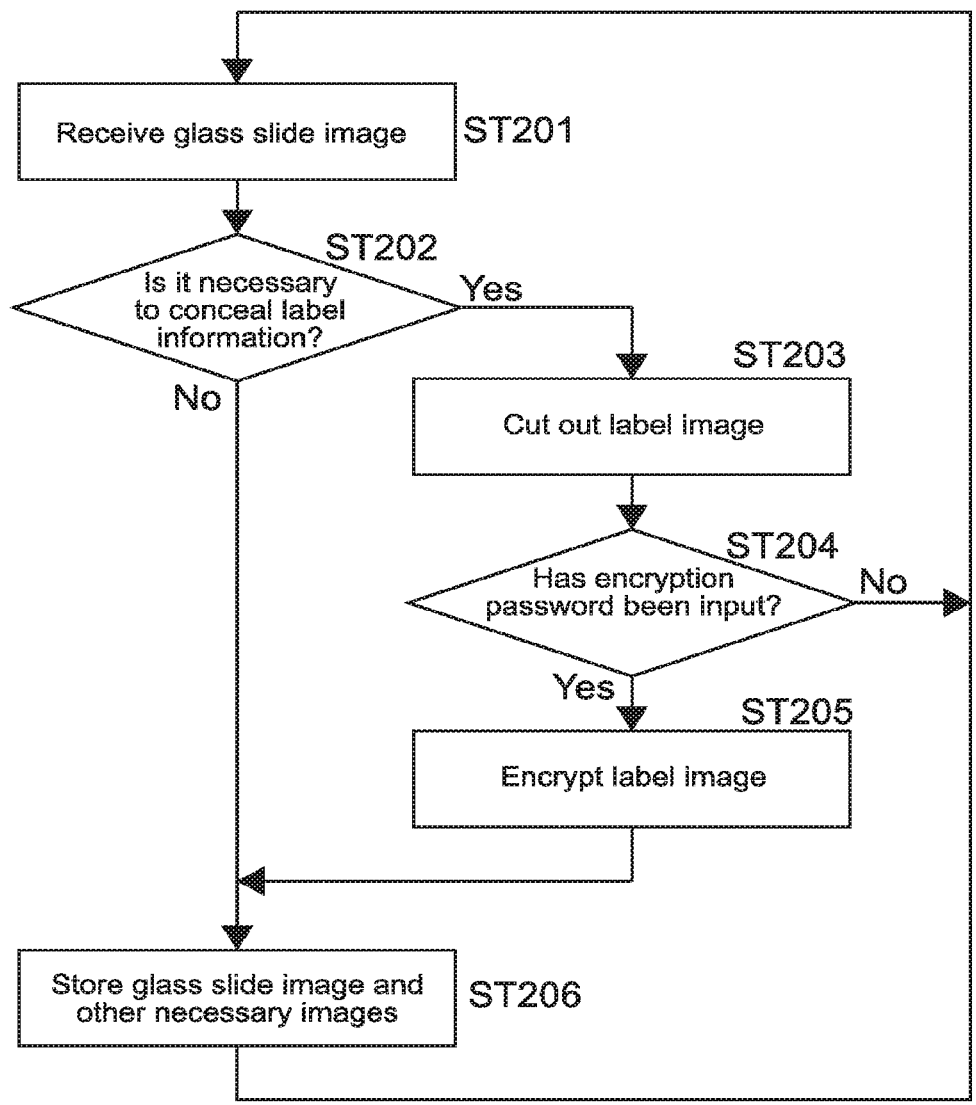
FIG. 10 is a flowchart showing a storage process for the case where a cutout label image can be encrypted.

Next, a storing process in the case where the cutout label image 26' is encrypted will be described. FIG. 10 is a flowchart showing the process.

The process of Steps 201 to 203 is the same as Steps 101 to 103 shown in FIG. 6.

The server 200 determines whether a password for the encryption is input or not (Step 204). For example, the scanner 300 only has to receive the input of the password by the user at a predetermined timing and transmit the password information to the server 200. The predetermined timing may be timing before or after the scanner 300 scans the glass slide SLG, for example.

In the case of No in Step 204, it may be impossible for the server 200 to encrypt the label image 26, so the label image may be deleted.

Figure 11A:
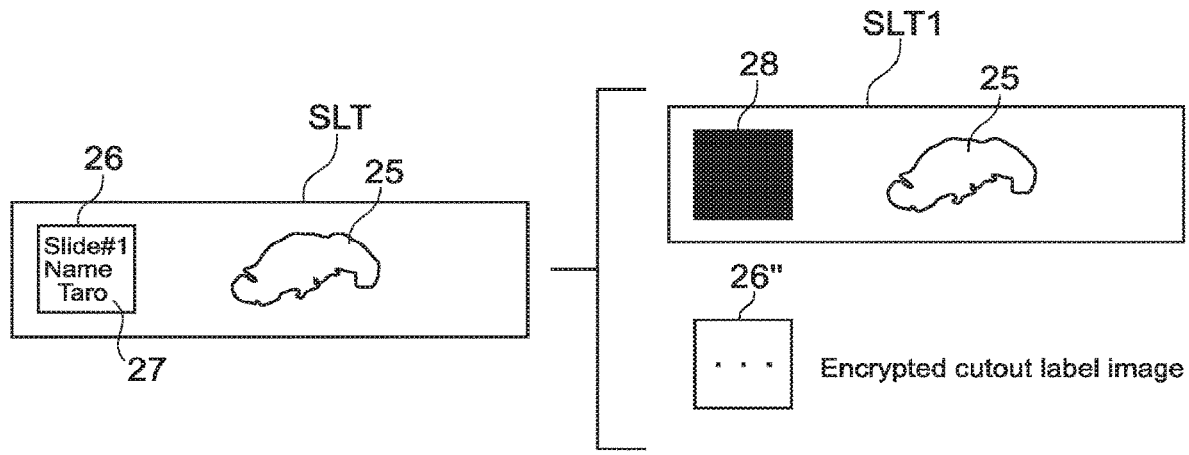
FIGS. 11A and 11B are diagrams corresponding to FIGS. 7 to 9 in the state where the label image is encrypted.
Figure 11B:
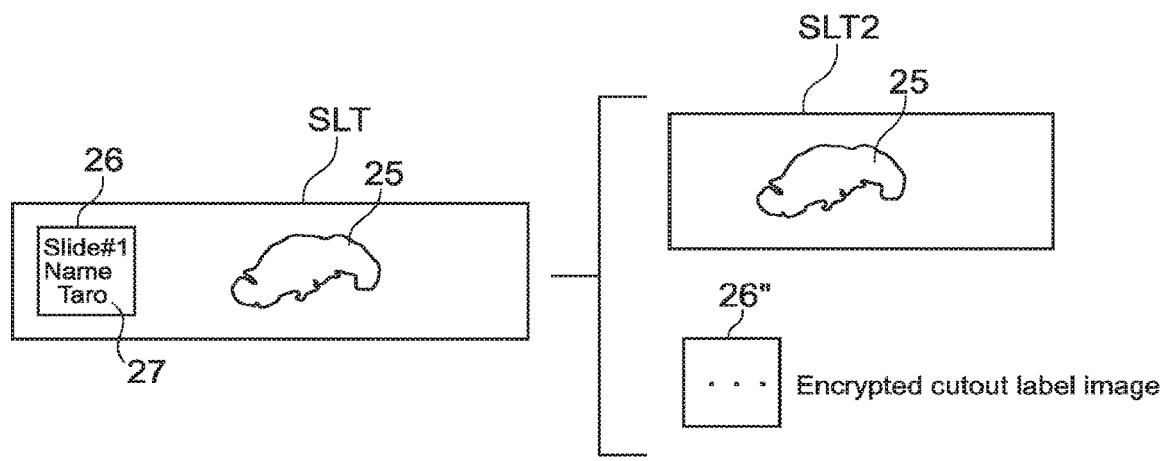

In the case of Yes in Step 204, the server 200 encrypts the label image 26, thereby obtaining an encrypted cutout label image 26" as shown in FIGS. 11A and 11B (Step 205). In the encryption process, an algorithm such as a DES (data encryption standard) and an AES (advanced encryption standard) may be used.

As described above, the server 200 stores the encrypted cutout label image 26" by one of the methods shown in FIGS. 7 to 9 (Step 206). Diagrams corresponding to FIGS. 7 and 8, respectively, are shown in FIGS. 11A and 11B.

2. Mode of Storing Glass Slide Image SLT by Scanner 300

In the above Item 1., the process in which the server 200 receives the glass slide image SLT transmitted from the scanner 300 and stores the image is described. In the Item 2., a mode of storing the glass slide image SLT by the scanner 300 will be described.

(A) Process in Case where Label Image is Not Encrypted

Figure 12:
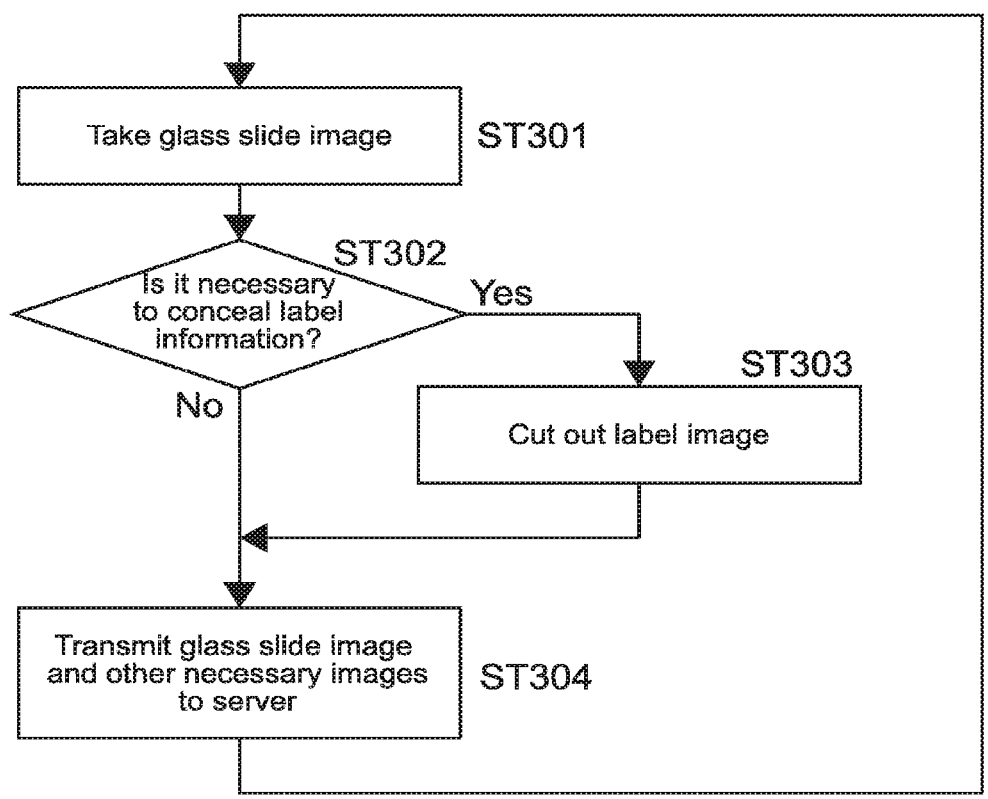
FIG. 12 is a flowchart showing a storage process for the case where the cutout label image is not encrypted.

FIG. 12 is a flowchart showing a storing process in the case where the cutout label image 26' is not encrypted as in the (A) of the Item 1. The storing process by the scanner 300 is basically the same as the storing process by the server 200.

The scanner 300 takes an image of the entire glass slide SLG separately from taking an image of the sample (generating real image data) as described above, thereby obtaining the glass slide image SLT including the label image 26 and the sample image 25 (Step 301). Then, the scanner 300 executes the same process as Step 102 shown in FIG. 6 (Step 302).

In the case of Yes in Step 302, the scanner 300 cuts out the label image 26 from the glass slide image SLT, thereby generating the cutout label image 26' (Step 303). An algorithm for the cutout process may be the algorithm described above.

The scanner 300 transmits the image generated to the server 200 (Step 304). In this case, the scanner 300 temporarily stores the image generated in the memory (storage unit) and outputs the image to the server 200 (output unit).

In Step 304, in the case of Yes in Step 302, the scanner 300 transmits the glass slide image SLT taken in Step 301 as the thumbnail image. On the other hand, in the case where the process goes through Step 303, the scanner 300 associates the cutout label image 26' and the label-removed glass slide image SLT1 (SLT2) with each other and transmits those images to the server 200 as the thumbnail images.

(B) Process in Case where Label Image is Encrypted

Figure 13:
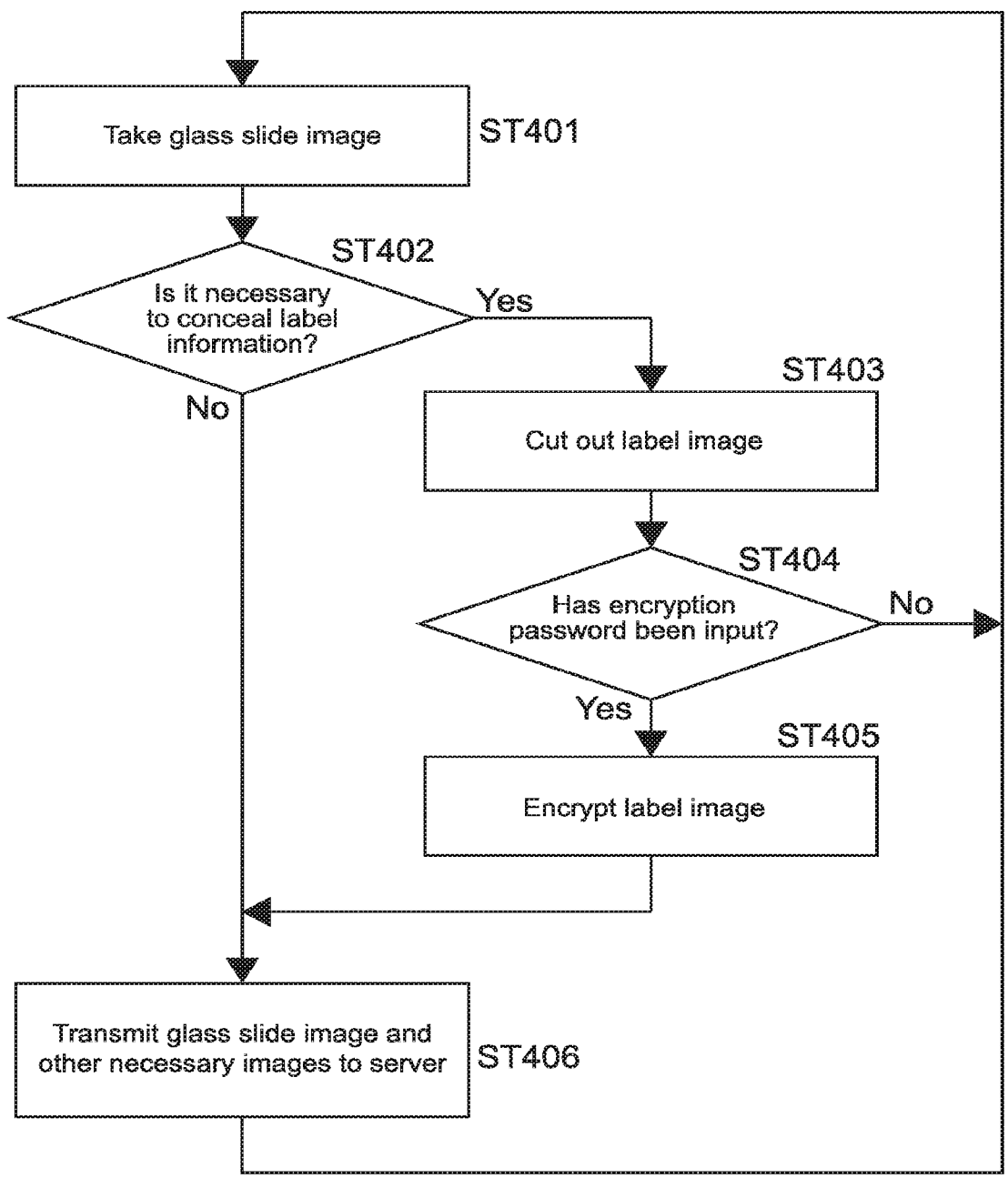
FIG. 13 is a flowchart showing a process in the case where the scanner encrypts the cutout label image.

FIG. 13 is a flowchart showing a process in the case where the scanner 300 encrypts the cutout label image 26'. The process is basically the same as the process shown in FIG. 10.

In Step 406, as shown in FIGS. 11A and 11B, the scanner 300 associates the cutout label image 26' encrypted and the label-removed glass slide image SLT1 or the like with each other and transmits those images to the server 200 as the thumbnail images.

(Process of Displaying Glass Slide Image SLT)

Figure 14:
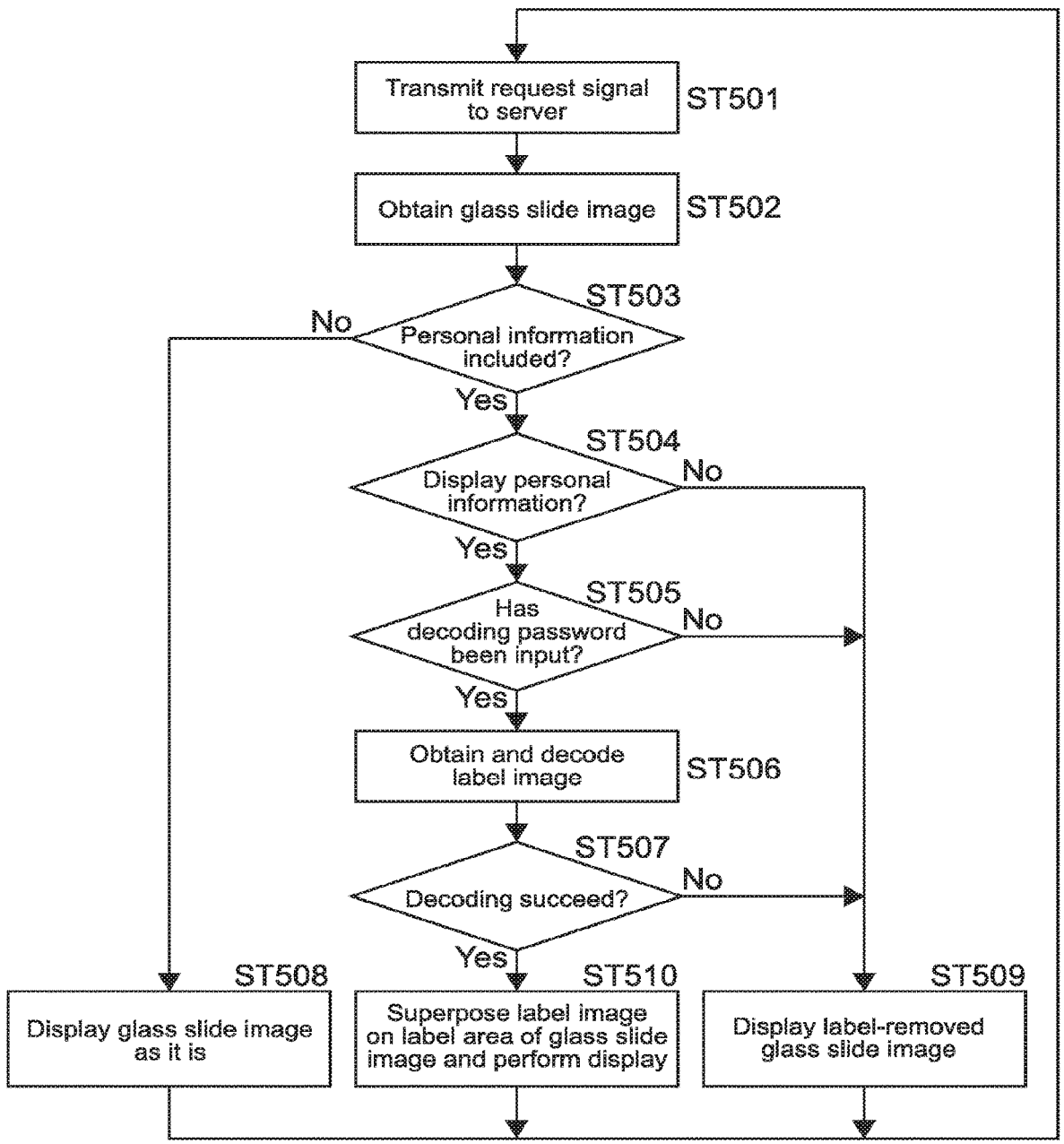
FIG. 14 is a flowchart showing a display process for a thumbnail image by a viewer.

Next, a process of displaying the thumbnail image by the viewer 100 will be described. FIG. 14 is a flowchart showing the process.

The viewer 100 requests the server 200 to obtain information of a file list for accessing and viewing the glass slide image SLT and the real image data (generates a request signal (generation unit) and output the signal to the server 200) (Step 501). That is, the viewer 100 mainly outputs a request signal for obtaining one or more glass slide images SLT. The viewer 100 may generate the request signal in accordance with an operation input by the user to the viewer 100 or may generate the signal in accordance with a predetermined algorithm.

Upon reception of the request signal, the server 200 transmits the one or more glass slide images SLT specified in the obtaining request. In the process, the server 200 transmits, to the viewer 100, the glass slide image SLT stored in one of the modes shown in FIGS. 7 to 9 and FIGS. 11A and 11B. In the process shown in FIG. 14, to help understanding the explanation, the following assumption is made. That is, a mode will be described in which the server 200 transmits various glass slide images or the like stored in the storage device thereof to the viewer 100, and the viewer 100 causes the glass slide images to be subject to various processes (for example, information encrypted is decoded) to be displayed on the basis of a predetermined algorithm.

Figure 15:
FIG. 15 is a diagram showing various modes of the glass slide image which can be displayed by the viewer in the case where the label image is not encrypted.
Figure 16:
FIG. 16 is a diagram showing various modes of the glass slide image which can be displayed by the viewer in the case where the label image is encrypted.

FIGS. 15 and 16 show various modes of the glass slide images SLT (including processed and non-processed images) that can be displayed by the viewer 100. In particular, FIG. 15 shows images in the case where the label image is not encrypted as described in the above Item 1. (A) or 2. (A). FIG. 16 shows images in the case where the label image is encrypted as described in the above Item 1. (B) or 2. (B). The glass slide image SLT (thumbnail image) to be displayed out of those images is changed depending on a result of the determination process of the flowchart shown in FIG. 14.

Upon obtaining (reception) of the glass slide image SLT (Step 502), the viewer 100 determines whether it is necessary to conceal the label information of the glass slide image SLT or not (Step 503). The process of Step 503 is the same as the "dynamic" process described in Step 102 shown in FIG. 6 or the like.

In the case of No in Step 503, the viewer 100 displays the glass slide image SLT received, that is, the original glass slide image SLT (image shown in the column A of FIG. 15) as the thumbnail image (Step 508). In this case, the CPU 101, the input and output interface 105, or the like of the viewer 100 functions as the output unit for outputting the thumbnail image to the display unit 106 (the same holds true for Steps 509 and 510 to be described later).

It should be noted that, even in the case of No in Step 503 and the case where the label image 26 is encrypted, the viewer 100 may decode the image and display the original glass slide image SLT (image shown in the column A of FIG. 16) in Step 508.

In the case of Yes in Step 503, the viewer 100 determines whether the image of the area (label area) where the label image 26 is provided in the glass slide image SLT is displayed or not (Step 504). A result of the determination process may be changed depending on the setting of application software held by the viewer 100, for example. For example, in the case where such a setting that the label area is not displayed is provided (No in Step 504), the label-removed glass slide image SLT1 (image shown in the column B of FIG. 15) is generated and displayed (Step 509). On the other hand, in the case of providing such a setting that the label area is displayed (Yes in Step 504), the process proceeds to Step 505, and the viewer 100 performs the process.

It should be noted that the image shown in the column C of FIG. 15 is the glass slide image SLT on which the label information including the personal information is described. In this way, the viewer may have such a setting that the glass slide image SLT can be displayed as the thumbnail image as it is without going through the process of Step 505 and the subsequent steps.

In Step 509, the server 200 may transmit the label-removed glass slide image SLT1 to the viewer 100, and the viewer 100 may receive and display the image (the same holds true for Step 510 to be described later).

In the case of Yes in Step 504, the viewer 100 determines whether a password for decoding the image has been input or not (Step 505). This is a determination process of whether the user has input a user ID and a password at a time of logging in the server 200 on the application software for viewing the image held by the viewer 100 or at a time of using the software, for example. Of course, each time the viewer 100 requests to display the image, a password input screen may be displayed to cause the user to input the password.

In Step 505, in the case where the password has not been input, the process proceeds to Step 509. In this case, the viewer 100 displays, as the thumbnail image, the glass slide image SLT (image shown in the column B of FIG. 16) obtained by superposing a picture of a key as the label-removed glass slide image SLT1. As a result, it is possible to clearly indicate that the label information is protected by being encrypted.

On the other hand, in the case where the password has already been input in Step 505, the viewer 100 obtains the cutout label image 26" encrypted including the label information from the server 200 and decodes the image by using the password (Step 506). In this case, the server 200 transmits, to the viewer 100, the cutout label image 26" (see, FIGS. 11A and 11B) encrypted and associated with the glass slide image SLT that have been transmitted.

In the case where the decoding is failed (No in Step 507), the viewer 100 then performs the process of Step 509 and displays, as the thumbnail image, the label-removed glass slide image (image shown in the column C of FIG. 16) obtained by superposing the picture of the key on the label area, as in the process in which the password has not been input. The case where the decoding is failed refers to the case where the password is incorrectly input, for example.

In the case where the decoding succeeds (Yes in Step 507), the viewer 100 superposes the decoded cutout label image 26' on the label area of the label-removed glass slide image, thereby restoring the original glass slide image SLT (image shown in the column D of FIG. 16). Then, the viewer 100 displays the restored original glass slide image SLT as the thumbnail image (Step 510).

Figure 17:
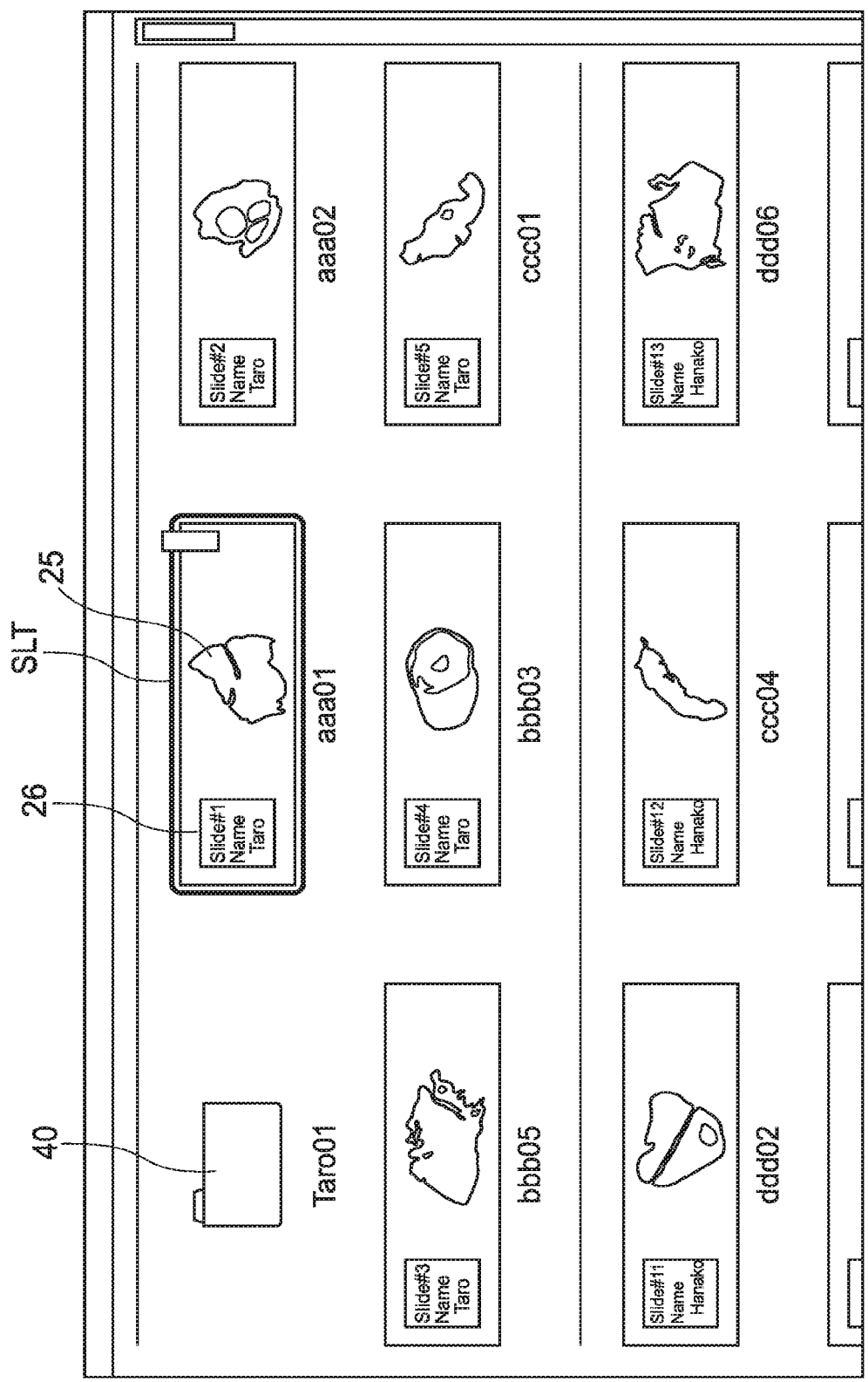
FIG. 17 is a diagram showing an example of a screen of a list of the thumbnail images displayed by the viewer.

FIG. 17 is a diagram showing an example of the screen of the list of the thumbnail images displayed by the viewer 100. In this example, for example, a plurality of glass slide image SLT are displayed as the thumbnail images in one folder 40, and the label image 26 is indicated in each of the glass slide images SLT. The user accesses (double-clicks, for example) the file of the thumbnail images, and the viewer 100 is triggered to request the server 200 to transmit the real image data corresponding thereto. Then, in response to this, the server 200 transmits the real image data to the viewer 100.

(Effect of Present Application)

As described above, according to the present disclosure, the glass slide image SLT including both of the sample image 25 and the label image 26 can be displayed as the thumbnail image. Thus, the user can view the actual glass slide SLG as it is on the screen. Therefore, an intuitive sense of the user is increased, and the convenience and the usability are improved. Specifically, the user can easily select a desired file.

Further, according to the present disclosure, it is possible to overcome the following problems.

Figure 18A:
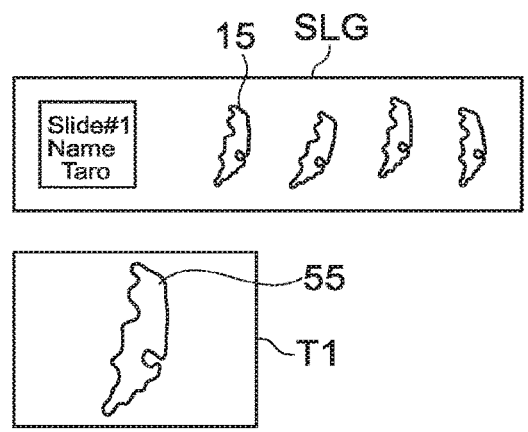
FIGS. 18A to 18C are diagrams showing actual glass slides and thumbnail images obtained from the glass slides by scanning according to reference examples compared to the present disclosure.
Figure 18B:
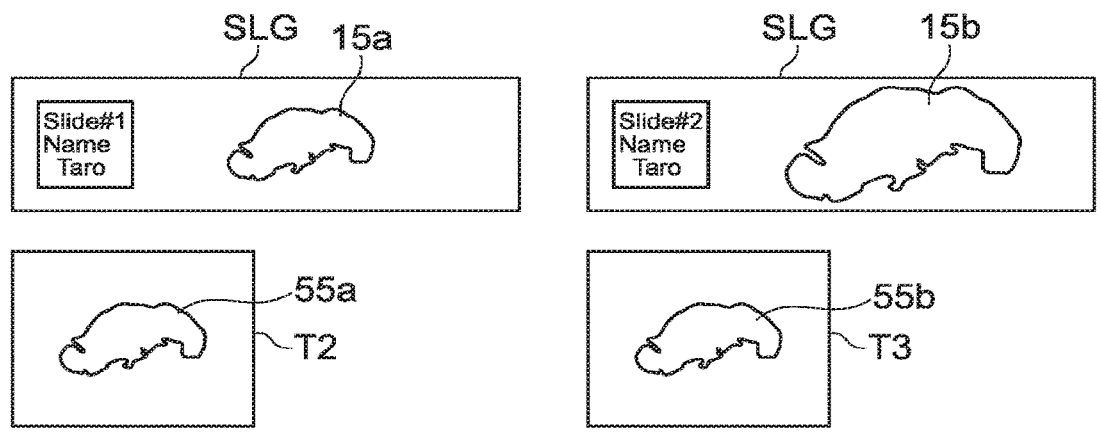
Figure 18C:
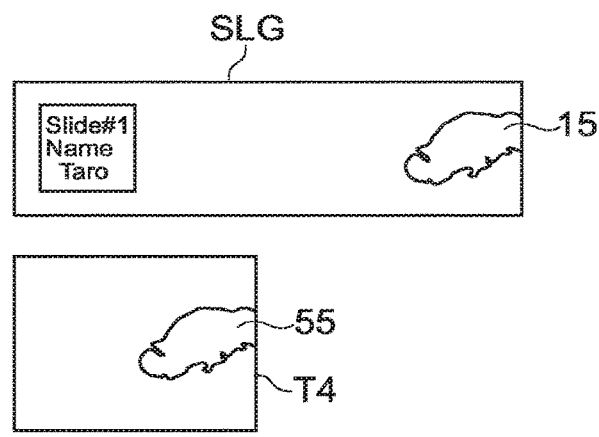

FIGS. 18A to 18C are diagrams each showing an actual glass slide SLG and a thumbnail image obtained by scanning the glass slide SLG according to a reference example compared to the present disclosure.

For example, in FIG. 18A, the samples 15 obtained by dividing the sample into continuous slices are stored on the glass slide SLG. A thumbnail image T1 is obtained by taking an image of one of the divided samples and converting the image into image data. In this case, it is difficult for the user to recognize one of the plurality of continuous slices of the samples 15 which is indicated by an image 55 of the sample displayed as the thumbnail image T1. Further, in some cases, it may be impossible for the user to recognize that the image 55 of the sample is obtained from the continuous slices. In contrast, according to the present disclosure, user can view the glass slide image SLT including both of the sample image 25 and the label image 26, with the result that it is possible to overcome the above problem.

As shown in FIG. 18B, for the plurality of glass slides SLG, a sample 15a and a sample 15b have different sizes, so when images of the samples are taken, different magnifications for image taking may be caused. But, as shown in the figure, if images 55a and 55b of the samples obtained as thumbnail images T2 and T3, respectively, have almost the same size when being displayed, it may be impossible for the user to compare the sizes of the samples in the case where those images have similar shapes.

As shown in FIG. 18C, in the case where the sample 15 stored on the actual glass slide SLG is cut off at the right end thereof, when the user views a thumbnail image T4, it is difficult for the user to determine whether a mistake in taking the image is made or the right end is actually cut off. For this reason, wasted re-scanning may has to be performed.

According to the present disclosure, it is possible to overcome the problems shown in FIGS. 18B and 18C. That is, the user views the thumbnail images before the real image data is displayed, and thus can confirm the size of the sample. Further, it is possible to prevent the wasted re-scanning from being performed.

Further, according to the present disclosure, as shown in FIGS. 7, 8, 11A, and 11B, for example, the label-removed glass slide image and the cutout label image 26' are stored separately in different files, which is useful for management of information.

According to the present disclosure, even in the case where the label information 17 includes the personal information and the like, the label image is encrypted, so if the label image data is copied, the leakage of the personal information can be prevented. As a result, the security can be enhanced.

For example, it is conceivable that, in selecting a file, the user performs switching between display and non-display of the label information collectively. However, only by this operation, it is difficult to prevent the leakage of the personal information. In contrast, in the present disclosure, it is possible to superpose the cover image 28 for the concealment on the label area, so the label image is not displayed as long as the label image encrypted is decoded. As a result, it is possible to enhance the security.

(Another Embodiment)

The present disclosure is not limited to the above embodiment and can have various other embodiments.

In the above embodiment, the scanner 300 irradiates the surface of the glass slide SLG with irradiation light and takes the image of the target by using reflection of the light. In addition, the scanner 300 may obtain a glass slide image SLT thus obtained, and may irradiate a back surface, which is the opposite side of the surface of the glass slide SLG, with the irradiation light and takes transmission light as a target image. Because the sample 15 stored on the glass slide SLG is sliced thinly to such an extent that the sample causes the irradiation light to pass therethrough, it is possible to take the image from the side of the front surface. On the other hand, the label area shows a shadow thereof because the label 16 is attached thereto, so the scanner 300 can obtain the label-removed glass slide image by taking an image thereof. In this case, the scanner 300 or the server 200 only has to store the normal glass slide image SLT and the label-removed glass slide image with those images associated with each other. According to this embodiment, an algorithm for the cutout process of the label image is unnecessary.

In the process shown in FIG. 14, the server 200 may perform the decoding process of Step 506, the superposing process of Step 510, and the like, and may transmit the glass slide image SLT obtained by the superposing process to the viewer 100.

The information processing apparatus according to this embodiment includes the scanner 300, the server 200, and the viewer 100. However, for example, the scanner 300 and the server 200 may be physically integrated with each other. In this case, the scanner 300 can store various images obtained by image taking in the storage device thereof and can also function as the server 200 that transmits the images to the viewer 100 in response to a request of the viewer 100.

In the above embodiment, in the case where the label information is read by the character recognition process, for example, and text information is created, the scanner 300 or the server 200 may encrypt the text information (label information) in addition to the process for encrypting the label image.

Out of the characteristic parts of the embodiments described above, at least two characteristic parts can be combined.

It should be noted that the present disclosure can take the following configurations.

(1) An information processing apparatus, including:

a storage unit capable of storing an image of a slide including both images of a sample and a label which are obtained by shooting the slide, the slide holding the sample and having a front surface on which the label indicating label information relating to the sample is provided; and an output unit capable of outputting the image of the slide as a thumbnail image.

(2) The information processing apparatus according to Item (1), further including a processing unit configured to generate a cutout label image by cutting out the label image in the slide image, in which the storage unit stores a label-removed slide image which includes at least the sample image in the slide image and is obtained by removing the label image therefrom and the cutout label image with the label-removed slide image and the cutout label image associated with each other.

(3) The information processing apparatus according to Item (2), in which the processing unit superposes a cover image for concealing the label image in the slide image on the label image in the slide image, thereby generating the label-removed slide image, and the storage unit stores the label-removed slide image and the cutout label image with the label-removed slide image and the cutout label image associated with each other.

(4) The information processing apparatus according to Item (2), in which the processing unit is capable of encrypting the cutout label image, and the storage unit stores the label-removed slide image and an encrypted cutout label image that is subjected to the encryption with the label-removed slide image and the encrypted cutout label image associated with each other.

(5) The information processing apparatus according to Item (3), in which the processing unit is capable of encrypting the cutout label image, and the processing unit stores the label-removed slide image and an encrypted cutout label image that is subjected to the encryption with the label-removed slide image and the encrypted cutout label image associated with each other.

(6) The information processing apparatus according to Item (4) or (5), in which the processing unit is capable of decoding the encrypted cutout label image on the basis of a decoding password, and superposes the cutout label image decoded on an area where the label is provided in the label-removed slide image to restore the slide image.

(7) The information processing apparatus according to Item (2), in which the processing unit superposes a cover image for concealing the label image in the slide image on the label image in the slide image, thereby generating the label-removed slide image, and the storage unit stores the label-removed slide image and the slide image which is original with the label-removed slide image and the original slide image associated with each other.

(8) The information processing apparatus according to Item (7), in which the output unit selectively outputs the original slide image and the label-removed slide image.

(9) The information processing apparatus according to any one of Items (2) to (8), in which the processing unit cuts out a predetermined area from the slide image as a label area.

(10) The information processing apparatus according to any one of Items (2) to (8), in which the processing unit cuts out the label image from the slide image by an edge detection process.

(11) The information processing apparatus according to Item (2), in which the processing unit reads the label information in the slide image by a character recognition process.

(12) The information processing apparatus according to Item (11), in which the processing unit encrypts the label information read.

(13) The information processing apparatus according to Item (1), in which when the slide is transparent, the storage unit stores the sample image and a label-removed slide image from which the label information is concealed with a shadow of the label with the sample image and the label-removed slide image associated with the slide image, the sample image and the label-removed slide image being obtained by irradiating the slide with illumination light from a back surface side, which is an opposite side to the front surface of the slide, and shooting the slide from the front surface side.

(14) An information processing system, including:

a scanner apparatus including an obtaining unit capable of shooting a slide that holds a sample and has a front surface on which a label indicating label information relating to the sample is provided and capable of obtaining an image of the slide, which includes both images of the sample and the label by the shooting, and a transmission unit capable of transmitting the image of the slide, a server apparatus including a storage unit capable of storing, as a thumbnail image, the slide image transmitted from the transmission unit of the scanner apparatus, a reception unit capable of receiving a request signal for requesting obtainment of the thumbnail image, and a transmission unit capable of transmitting the stored thumbnail image on the basis of the reception of the request signal; and a viewer apparatus including
a generation unit capable of generating the request signal,
a transmission unit capable of transmitting the request signal generated to the server apparatus, and
a reception unit capable of receiving the thumbnail image transmitted from the server apparatus.

(15) An information processing system, including:
a server apparatus including
a storage unit capable of storing, as a thumbnail image, an image of a slide including both images of a sample and a label which are obtained by shooting the slide, the slide holding the sample and having a front surface on which the label indicating label information relating to the sample is provided,
a reception unit capable of receiving a request signal for requesting obtainment of the thumbnail image, and
a transmission unit capable of transmitting the stored thumbnail image on the basis of the reception of the request signal; and
a viewer apparatus including
a generation unit capable of generating the request signal,
a transmission unit capable of transmitting the request signal generated to the server apparatus, and
a reception unit capable of receiving the thumbnail image transmitted from the server apparatus.

(16) An information processing method, including:
storing, as a thumbnail image, an image of a slide including both images of a sample and a label which are obtained by shooting the slide, the slide holding the sample and having a front surface on which the label indicating label information relating to the sample is provided; and
outputting the thumbnail image.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An image processing apparatus, comprising:
circuitry configured to
obtain a slide image including a sample area and a label area, wherein the sample area and the label area are two different parts of the slide image;
identify the label area and the sample area based on an image processing process to the slide image;
generate a cutout image of the label area;
generate a label-removed image including the slide image having a cover image superposed over the label area;
store the cutout image and the label-removed image; and
output at least one of the sample area of the slide image or an information identified from the label area.

2. The apparatus according to claim 1, wherein the slide image is an image captured by a microscope.

3. The apparatus according to claim 1, wherein the slide image is an image of at least one of cells, tissues, or organs.

4. The apparatus according to claim 1, wherein the label area indicates label information relating to the sample.

5. The apparatus according to claim 4, wherein the label information includes at least one of an identifier for identifying a patient of the slide image, stain information, information that indicates an examination date and time of a patient, or a scanning date and time.

6. The apparatus according to claim 4, wherein the label information is personal information of a patient of the slide image.

7. The apparatus according to claim 1, wherein the circuitry is further configured to encrypt the label area.

8. The apparatus according to claim 7, wherein the circuitry is further configured to decode the encrypted label area.

9. An image processing method, comprising:
obtain a slide image including a sample area and a label area, wherein the sample area and the label area are two different parts of the slide image;
identify the label area and the sample area based on an image processing process to the slide image;
generate a cutout image of the label area;
generate a label-removed image including the slide image having a cover image superposed over the label area;
store the cutout image and the label-removed image; and
output at least one of the sample area of the slide image or an information identified from the label area.

10. An image processing system, comprising:
an image capturing device configured to capture a slide image including a sample area and a label area, wherein the sample area and the label area are two different parts of the slide image;
a memory executable code which, when read causes a processor to:
identify the label area and the sample area based on an image processing process to the slide image;
generate a cutout image of the label area;
generate a label-removed image including the slide image having a cover image superposed over the label area;
store the cutout image and the label-removed image; and
cause a display device to display at least one of the sample area of the slide image or an information identified from the label area.

11. The apparatus according to claim 1, wherein the image processing process includes an edge detection process or a character recognition process.

12. The method according to claim 9, wherein the image processing process includes an edge detection process or a character recognition process.

13. The system according to claim 10, wherein the image processing process includes an edge detection process or a character recognition process.

* * * * *